US011236067B2

(12) United States Patent
Singh

(10) Patent No.: US 11,236,067 B2
(45) Date of Patent: Feb. 1, 2022

(54) COMPOUND FOR TREATING CYSTIC FIBROSIS

(71) Applicant: ORPHOMED, INC., Mill Valley, CA (US)

(72) Inventor: Nikhilesh Nihala Singh, Mill Valley, CA (US)

(73) Assignee: OrphoMed, Inc., Mill Valley, CA (US)

( * ) Notice: Subject to any disclaimer, the term of this patent is extended or adjusted under 35 U.S.C. 154(b) by 0 days.

(21) Appl. No.: 16/925,439

(22) Filed: Jul. 10, 2020

(65) Prior Publication Data

US 2021/0009556 A1     Jan. 14, 2021

Related U.S. Application Data

(60) Provisional application No. 62/873,556, filed on Jul. 12, 2019.

(51) Int. Cl.
| | | |
|---|---|---|
| *C07D 401/12* | (2006.01) | |
| *A61K 31/44* | (2006.01) | |
| *A61K 9/00* | (2006.01) | |
| *A61K 9/20* | (2006.01) | |

(52) U.S. Cl.
CPC .......... *C07D 401/12* (2013.01); *A61K 9/0053* (2013.01); *A61K 9/20* (2013.01); *A61K 31/44* (2013.01)

(58) Field of Classification Search
CPC combination set(s) only.
See application file for complete search history.

(56) References Cited

U.S. PATENT DOCUMENTS

| | | | |
|---|---|---|---|
| 8,999,976 B2 | 4/2015 | Binch et al. | |
| 9,012,496 B2 | 4/2015 | Alargova et al. | |
| 9,309,256 B2 | 4/2016 | Singh | |
| 9,321,780 B2 | 4/2016 | Singh | |
| 9,480,665 B2 | 11/2016 | Singh | |
| 9,549,924 B2 | 1/2017 | Singh | |
| 9,732,096 B2 | 8/2017 | Singh | |
| 9,782,369 B2 | 10/2017 | Singh | |
| 2012/0309758 A1 | 12/2012 | Sheth et al. | |
| 2015/0231142 A1 | 8/2015 | Van Goor et al. | |
| 2016/0120841 A1 | 5/2016 | Kym et al. | |
| 2016/0122331 A1 | 5/2016 | Kym et al. | |
| 2017/0015675 A1 | 1/2017 | Altenbach et al. | |
| 2017/0035709 A1 | 2/2017 | Singh | |
| 2017/0101405 A1 | 4/2017 | Akkari et al. | |
| 2017/0101406 A1 | 4/2017 | Akkari et al. | |
| 2017/0305891 A1 | 10/2017 | Altenbach et al. | |
| 2018/0099931 A1 | 4/2018 | Altenbach et al. | |
| 2018/0099932 A1 | 4/2018 | Altenbach et al. | |

FOREIGN PATENT DOCUMENTS

| | | |
|---|---|---|
| WO | 2005/120497 A2 | 12/2005 |
| WO | 2005/120497 A3 | 12/2005 |
| WO | 2006/002421 A2 | 1/2006 |
| WO | 2006/002421 A3 | 1/2006 |
| WO | 2008/147952 A1 | 12/2008 |
| WO | 2009/074575 A2 | 6/2009 |
| WO | 2009/074575 A3 | 6/2009 |
| WO | 2009/076593 A1 | 6/2009 |
| WO | 2010/048573 A1 | 4/2010 |
| WO | 2011/072241 A9 | 6/2011 |
| WO | 2011/113894 A1 | 9/2011 |
| WO | 2012/048181 A1 | 4/2012 |
| WO | 2012/048181 A4 | 4/2012 |
| WO | 2013/038373 A1 | 3/2013 |
| WO | 2013/038378 A1 | 3/2013 |
| WO | 2013/038381 A1 | 3/2013 |
| WO | 2013/038386 A1 | 3/2013 |
| WO | 2013/038390 A1 | 3/2013 |
| WO | 2013/043720 A1 | 3/2013 |
| WO | 2014/180562 A1 | 11/2014 |
| WO | 2015/018823 A1 | 2/2015 |
| WO | 2015/138909 A1 | 9/2015 |
| WO | 2015/138934 A1 | 9/2015 |
| WO | 2016/193812 A1 | 12/2016 |
| WO | 2017/208115 A1 | 12/2017 |

OTHER PUBLICATIONS

International Search Report dated Oct. 9, 2020 corresponding to PCT/US2020/041490 filed Jul. 10, 2020; 6 pages.

*Primary Examiner* — Heidi Reese

(74) *Attorney, Agent, or Firm* — Mintz Levin Cohn Ferris Glovsky and Popeo PC

(57) ABSTRACT

Provided herein is a compound represented by Formula I:

(I)

or a pharmaceutically acceptable salt, hydrate, solvate or complex thereof. Also provided are pharmaceutical compositions comprising the compound noted above, in combination with a pharmaceutically acceptable excipient.

14 Claims, 2 Drawing Sheets

Compound 10 normalized for solubility

COMPOUND FOR TREATING CYSTIC FIBROSIS

CROSS-REFERENCES TO RELATED APPLICATIONS

This is an application claiming priority benefit under 35 U.S.C. § 119(e) of U.S. Provisional Application No. 62/873,556 filed on Jul. 12, 2019, which is herein incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Cystic fibrosis (CF) is the most common fatal genetic disease among Caucasians. Although the clinical features of cystic fibrosis involve multiple organs, the primary cause of morbidity and mortality is chronic pulmonary infections. Cystic fibrosis is caused by mutations in a single gene: the cystic fibrosis transmembrane regulator (CFTR). CFTR controls transport of multiple ions responsible for proper hydration and the anti-inflammatory and/or antimicrobial defense of mucosal surfaces throughout the body. Loss of CFTR function results in accumulation of viscous secretions and repeated lung infections, and accordingly cystic fibrosis airways are highly susceptible to microbial infection and inflammation while non-CF airways are resistant. As CF is a disease resulting from mutations in a single gene, the dramatic CF vs non-CF represent loss of functions directly attributable to and controlled by CFTR.

Currently there is no effective drug to prevent the disease progression associated with most CF mutations. Standard CF therapy relies heavily on repeated use of antibiotics that ultimately fail to eradicate lung infection and lead to emergence of multi-drug resistant pathogens. Decline in lung function among CF patients is seen even in early childhood, and leads to requirement for lung transplant or premature death by respiratory failure.

Among substrates known to be dependent, entirely or in part, on CFTR for transport to mucosal surfaces are glutathione, bicarbonate and thiocyanate, all of which serve critical roles in airways defense against inflammation and infection. These findings of transport dependence of multiple large multi-atomic ions by CFTR should not be surprising, as cloning and sequencing of CFTR in 1989 revealed that CFTR is a member of the ABC transporter gene family.

Gene products of the ABC transporter family actively transport multi-atomic molecules across a membrane in one direction using the energy of ATP to do the 'pumping'. Originally, CFTR was believed to function mainly as a chloride channel. However, there are some CFTR mutations, called chloride-conducting mutants, which move chloride ions normally but still cause CF disease. If patients can move chloride ions through CFTR normally and still have severe and progressive CF lung disease, this must mean that transport of the multi-atomic substrates by CFTR (such as bicarbonate, glutathione, and thiocyanate), in other words the ABC transporter functions of CFTR, are essential to defense against inflammation and infection.

Reduction in inflammation is often associated with improved lung function even in normal individuals. Patients on statins, which are known to be anti-inflammatory, show less age related lung function decline than age matched controls not taking statins. Subsequently it has been shown that use of statins among lung transplant patients is associated with better graft survival and function.

In addition to providing anti-inflammatory benefits, compositions resulting from this invention include ingredients demonstrated to be CFTR modulators. CFTR may be a useful therapeutic target for mucosal surface diseases other than CF, such as COPD, chronic bronchitis, pancreatitis, asthma and irritable bowel syndrome (IBS). There is growing evidence that other inflammatory lung diseases such as COPD and chronic bronchitis may be caused by acquired CFTR deficiency through damage of the epithelial surface where CFTR resides; this absence of functional CFTR contributes to the disease process. As a result, compositions directed to CFTR modulation can improve health outcomes for lung disease with an inflammatory component where other strictly anti-inflammatory treatment approaches have failed.

Still further, defective or insufficient CFTR may be 'corrected' (restored to the cell surface) or 'potentiated' (increased in activity) by a variety of natural molecules derived from plants. Alternatively, synthetic molecules may be used. Plant-derived polyphenolic compounds have been indicated as CFTR modulating molecules due to lower risk of toxicity. Molecules may be provided by oral administration in an amount and combination effective to cause correction and/or potentiation of CFTR at the tissue site in need of treatment.

Combinations of several modulators (correctors and/or potentiators and/or amplifiers) are known in the art to be more efficacious than any single molecule to modulate CFTR function, although some single molecules may serve both to correct and potentiate CFTR. Ideally, a single therapeutic agent would be desirable for the effective treatment of CF. The present invention addresses this need—and others described herein.

BRIEF SUMMARY OF THE INVENTION

In one aspect, provided herein is a compound represented by Formula I:

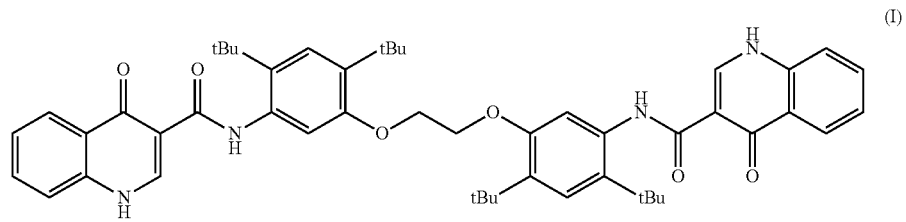 [SMILES: CC(C)(C)c1cc(C(C)(C)C)c(OCCOc2cc(NC(=O)c3c[nH]c4ccccc4c3=O)c(C(C)(C)C)cc2C(C)(C)C)cc1NC(=O)c1c[nH]c2ccccc2c1=O]

or a pharmaceutically acceptable salt, hydrate, solvate or complex thereof. Also provided are pharmaceutical compositions comprising the compound noted above, in combination with a pharmaceutically acceptable excipient.

In a related aspect, a method of treating cystic fibrosis in a subject in need thereof, is also provided. In this method an effective amount of a compound as recited above, or a composition comprising the compound above is administered to the subject—in an amount sufficient to alleviate at least some of the subject's symptoms of cystic fibrosis.

In a related aspect, a method of treating pancreatic insufficiency, Sjogren's Syndrome (SS), chronic obstructive lung disease (COLD), or chronic obstructive airway disease (COAD) in a subject in need thereof, is also provided. In this method an effective amount of a compound as recited above, or a composition comprising the compound above is administered to the subject—in an amount sufficient to alleviate at least some of the subject's symptoms of one or more of the recited diseases or conditions.

In other related aspects, combinations and methods of combination therapy are provided wherein the compound of Formula I is used in combination with a CFTR modulator, corrector, potentiator, amplifier, stabilizer, and/or an epithelial sodium channel blocker (ENaC)

DETAILED DESCRIPTION OF THE INVENTION

Definitions

Figure 1A:
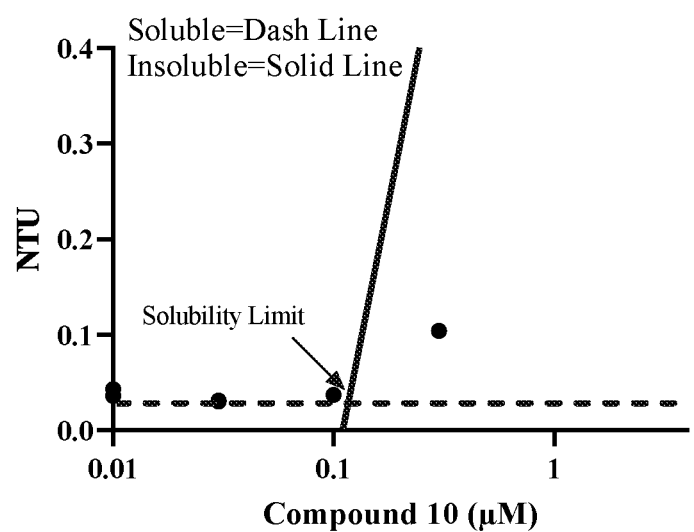
FIG. 1A and FIG. 1B show solubility and turbidity plots of the compound of Formula I (Compound 10) and ivacaftor, respectively.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of the compound of Formula I, or a pharmaceutical composition comprising same, to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering the compound of Formula I or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering the compound of Formula I or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of the compound of Formula I (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G, G1349D, S1251N, G178R, S549N mutations. More particularly, Class III mutation(s) refers to G551D, R553G, G1349D, S1251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10 kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326dellTC, or 4279insA mutations. More particularly, Class VI mutation(s) refers to Rescued F508del mutations.

Compound of Formula I—General

Provided herein is a compound of Formula I,

Thus, in specific embodiments, a pharmaceutically acceptable salt of the compound of Formula I (i.e., any pharmaceutically acceptable salt of the compound) is used in the methods of the invention. These salts can be prepared, for example, in situ during the final isolation and purification of the compound or by separately reacting the purified compound in its free base form with a suitable organic or inorganic acid and isolating the salt thus formed. In some embodiments, the pharmaceutically acceptable salt of the compound of Formula I is prepared using acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid. For further description of pharmaceutically acceptable salts that can be used in the methods described herein see, for example, S. M. Berge et al., "Pharmaceutical Salts," 1977, *J Pharm. Sci.* 66:1-19, which is incorporated herein by reference in its entirety.

The compound of Formula I can exist in unsolvated as well as solvated forms with pharmaceutically acceptable solvents such as water, ethanol, and the like. In general, the solvated forms are considered equivalent to the unsolvated forms for the purposes of the present invention. In a specific embodiment, the solvated form of the compound of Formula I is a hydrate.

In general, salt formation may improve shelf life of the resultant therapeutic agent. Appropriate salt synthesis can

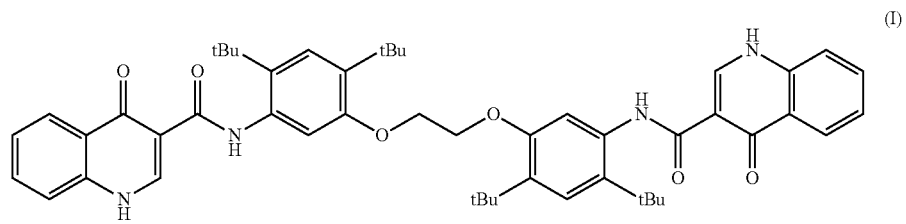 [SMILES: CC(C)(C)c1cc(C(C)(C)C)c(OCCOc2cc(NC(=O)c3c[nH]c4ccccc4c3=O)c(C(C)(C)C)cc2C(C)(C)C)cc1NC(=O)c1c[nH]c2ccccc2c1=O]

(I)

or a pharmaceutically acceptable salt, hydrate, solvate or complex thereof.

The compound represented by Formula I or a pharmaceutically acceptable salt, hydrate, solvate or complex is chemically and metabolically stable, when evaluated as a substrate in the presence of human liver microsomes. The compound of Formula I was also found not to substantially metabolize to ivacaftor, hydroxymethyl-ivacaftor or ivacaftor-carboxylate.

Pharmaceutical Compositions of the Compound of Formula I—General

In certain embodiments, provided herein are pharmaceutical compositions comprising the compound of Formula I. A pharmaceutical composition can further comprise a pharmaceutically acceptable carrier. Illustrative pharmaceutically acceptable carriers and formulations are described below.

As will be appreciated, a pharmaceutically acceptable salt of the compound of Formula I may be used instead of or in addition to the compound of Formula I in any or all of the compositions and methods of treating discussed herein.

afford products that are crystalline, less prone to oxidation and easy to handle. Various salts can be prepared that would afford stable and crystalline compounds. A few examples are hydrochloric, sulfuric, p-toluenesulfonic, methanesulfonic, malonic, fumaric, and ascorbic acid salts.

In certain specific embodiments, such a pharmaceutical composition is formulated as oral tablet or capsule, extended release oral tablet or capsule (hard gelatin capsule, soft gelatin capsule), sublingual tablet or film, or extended release sublingual tablet or film. Illustrative pharmaceutically acceptable carriers and formulations are described in more detail below.

Pharmaceutical Composition Forms, Dosing and Routes of Administration

The compound of Formula I provided herein can be administered to a subject orally in the conventional form of preparations, such as capsules, microcapsules, tablets, granules, powder, troches, pills, suppositories, oral suspensions, syrups, oral gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol).

Methods of Use

The compound of Formula I and compositions using any amount and any route of administration may be administered to a subject for the treatment or prevention of cystic fibrosis, pancreatic insufficiency, Sjogren's Syndrome (SS), chronic obstructive lung disease (COLD), or chronic obstructive airway disease (COAD).

The compound of Formula I is useful as a modulator of CFTR. Accordingly, the compound and compositions thereof are particularly useful for treating or lessening the severity or progression of a disease, disorder, or a condition where hyperactivity or inactivity of CFTR is involved. Thus, the invention provides a method for treating cystic fibrosis in a subject, wherein the method comprises administering to said subject a therapeutically effective amount of a compound of Formula I, with or without a pharmaceutically acceptable carrier. More particularly, the method provided herein is for the treatment or prevention of cystic fibrosis. In a more particular embodiment, the cystic fibrosis is caused by a Class I, II, III, IV, V, and/or VI mutation.

In another embodiment, the present invention provides the use of a compound of Formula I, or a pharmaceutically acceptable salt thereof, in the preparation of a medicament. The medicament optionally can comprise one or more additional therapeutic agents. In some embodiments, the medicament is for use in the treatment of cystic fibrosis. In a more particular embodiment, the cystic fibrosis is caused by a Class I, II, III, IV, V, and/or VI mutation.

In a related embodiment, the present invention is directed to the use of a compound of Formula I, or a pharmaceutically acceptable salt thereof, in the manufacture of a medicament for the treatment of cystic fibrosis, which optionally can comprise one or more additional therapeutic agents.

Combination Therapy

In another aspect, the present invention provides pharmaceutical compositions comprising a compound of Formula I, or a pharmaceutically acceptable salt thereof, and one or more additional therapeutic agents. In another embodiment, the present invention provides pharmaceutical compositions comprising a compound of the invention, or a pharmaceutically acceptable salt thereof, and one or more additional therapeutic agents wherein the additional therapeutic agents is another CFTR modulators.

Without intending to be bound by theory (or general characterization of a compound's function), a CFTR modulator can include activity associated with CFTR potentiation, correction, amplification, or combinations thereof.

A CFTR potentiator is a compound that assists chloride flow through the CFTR protein channel at the cell surface. The CFTR potentiator holds the channel open, allowing chloride ion to pass through and reduce symptoms of cystic fibrosis. An example of a CFTR potentiator is ivacaftor.

A CFTR corrector assists the CFTR protein with adopting the correct three dimensional shape so that the protein can move (or traffic) to the cell surface. A number of individuals with cystic fibrosis have two copies of the F508del mutation (or other similar mutations). This mutation prevents the CFTR protein from adopting the structure necessary for effective trafficking. CFTR correctors, such as lumacaftor and tezacaftor, help the protein conform to an appropriate shape, move to the cell surface, and remain on the cell surface longer. However, by themselves, these drugs are generally insufficient to reduce symptoms of cystic fibrosis and must be used as part of a combination treatment regimen.

A CFTR amplifier increases the amount of CFTR protein made by a cell. By increasing the amount of CFTR protein that is made, the potentiators and correctors become more effective in their individual roles.

As noted herein, the compound of Formula I or a pharmaceutically acceptable salt thereof may be administered as the sole active agent or it may be co-administered with other therapeutic agents, including other compounds or a pharmaceutically acceptable salt thereof that demonstrate the same or a similar therapeutic activity and that are determined to be safe and efficacious for such combined administration. The term "co-administered" refers to the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compound of Formula I or a pharmaceutically acceptable salt thereof may be co-administered with a therapeutically effective amount of one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors, and CFTR amplifiers).

In one embodiment, the compound of Formula I or a pharmaceutically acceptable salt thereof may be co-administered with one or two CFTR modulators. In one embodiment, the compound of Formula I or a pharmaceutically acceptable salt thereof may be co-administered with a CFTR amplifier. In one embodiment, the compound of Formula I or a pharmaceutically acceptable salt thereof may be co-administered with a CFTR corrector. In one embodiment, the compound of Formula I or a pharmaceutically acceptable salt thereof may be co-administered with a CFTR potentiator.

In another embodiment, the compound of Formula I or a pharmaceutically acceptable salt thereof may be co-administered with one CFTR potentiator, one or more CFTR correctors, and one CFTR amplifier. In still another embodiment, the compound of Formula I or a pharmaceutically acceptable salt thereof may be co-administered with one CFTR potentiator and one or more CFTR correctors. In yet another embodiment, the compound of Formula I or a pharmaceutically acceptable salt thereof may be co-administered with one CFTR potentiator and two CFTR correctors. In yet another embodiment, the compound of Formula I or a pharmaceutically acceptable salt thereof may be co-administered two CFTR correctors. In still another embodiment, the compound of Formula I or a pharmaceutically acceptable salt thereof may be co-administered with one or more CFTR correctors, and one CFTR amplifier. In one embodiment, the compound of Formula I or a pharmaceutically acceptable salt thereof may be co-administered with one CFTR corrector, and one CFTR amplifier.

Suitable agents to be used in these combination can be selected from the following: CFTR potentiators including, but not limited to, Ivacaftor, GLPG2451, GLPG1837, CTP-656, NVS-QBW251, FD1860293, PTI-808, N-(3-carbamoyl-5,5,7,7-tetramethyl-5,7-dihydro-4H-thieno[2,3-c]pyran-2-yl)-1H-pyrazole-5-carboxamide, and 3-amino-N-[(2S)-2-hydroxypropyl]-5-{[4-(trifluoromethoxy)-phenyl]sulfonyl}-pyridine-2-carboxamide. Other examples of CFTR potentiators are disclosed in: WO2005120497, WO2008147952, WO2009076593, WO2010048573, WO2006002421, WO2008147952, WO2011072241, WO2011113894, WO2013038373, WO2013038378, WO2013038381, WO2013038386, WO2013038390, WO2014/180562, WO2015018823, WO2016193812 and WO2017208115. Non-limiting examples of CFTR correctors include Lumacaftor, 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2222, GLPG2665, GLPG2737, GLPG2851, GLPG3221, PTI-801, VX-152, VX-440, VX-659, VX-445, FDL169, FDL304, FD2052160, and FD2035659. Examples of correctors are also disclosed in U.S. application Ser. Nos. 14/925,649, 14/926,727, 15/205,512, 15/496,094, 15/287,922, 15/287,911, 15/723,896 and 15/726,075.

In one embodiment, the additional therapeutic agent is a CFTR amplifier. Examples of CFTR amplifiers include PTI130 and PTI-428. Examples of CFTR amplifiers are also disclosed in International Patent Publication Nos.: WO2015138909 and WO2015138934.

In one embodiment, the additional therapeutic agent is a CFTR stabilizer. CFTR stabilizers enhance the stability of corrected CFTR that has been treated with a corrector, corrector/potentiator or other CFTR modulator combination(s). An example of a CFTR stabilizer is cavosonstat (N91115). Examples of stabilizers are also disclosed in International Patent Publication No.: WO2012048181.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Examples of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) are disclosed, for example, in International Patent Publication Nos.: WO2009074575 and WO2013043720; and U.S. Pat. No. 8,999,976.

EXAMPLES

Example 1: Synthetic Scheme for the Compound of Formula I (Compound 10)

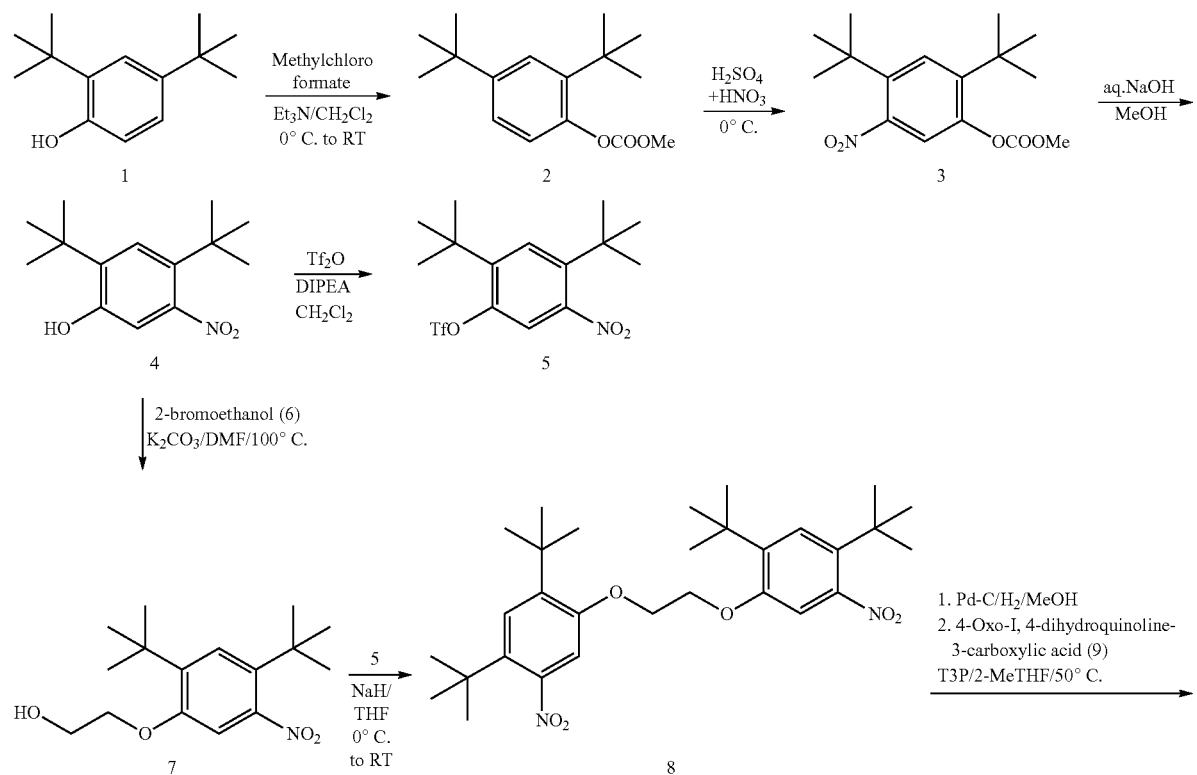

-continued

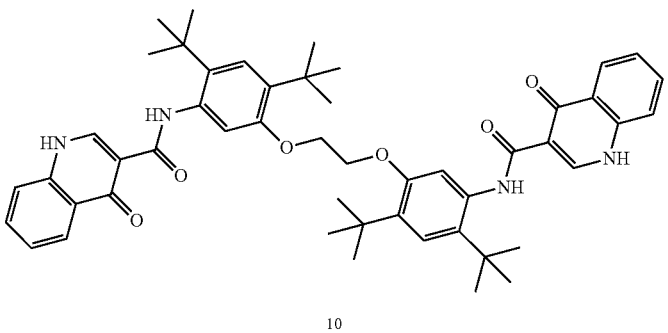

10

Preparation of Compound 2 (2,4-di-tert-butylphenyl methyl carbonate)

To a solution of 2,4-di-tert-butyl phenol, 1, (10 g, 48.5 mmol) in anhydrous dichloromethane (50 mL) and triethylamine (10.1 mL, 72.8 mmol), was added methyl chloroformate, (7.46 mL, 97 mmol) dropwise at 0° C. The mixture was then allowed to warm to room temperature and the reaction was stirred overnight. The reaction mixture was diluted with dichloromethane (100 mL) and washed with water (1×100 mL) and then brine (1×100 mL). The organic phase was dried over anhydrous sodium sulfate and concentrated to produce a yellow oil which was purified using column chromatography to give compound 2 (13 g, quant). $^1$H NMR (400 MHz, CDCl$_3$) δ7.41 (d, J=2.4 Hz, 1H), 7.26 (dd, J=8.4, 2.4 Hz, 1H), 7.03 (d, J=8.5 Hz, 1H), 3.92 (s, 3H), 1.39 (s, 9H), 1.34 (s, 9H).

Preparation of Compound 3 (2,4-di-tert-butyl-5-nitrophenyl methyl carbonate)

To a stirred solution of compound 2 (6.77 g, 25.6 mmol) was added 6 mL of a 1:1 mixture of sulfuric acid and nitric acid at 0° C. dropwise over 30 min while maintaining the internal temperature of the reaction below 5° C., and was then stirred at this temperature for an additional 2 hours. The reaction mixture was then slowly added to cold water, maintaining a temperature below 5° C. The quenched reaction was then heated to RT and the aqueous layer was removed and extracted with dichloromethane. The combined organic layers were washed with water, dried over Na$_2$SO$_4$, and concentrated to 10-15 mL. Hexane (50 mL) was added and the resulting mixture was again concentrated to 10-15 mL. More hexane (50-60 mL) was added to the mixture and then stirred for 16 hours, and was then filtered. To the filter cake was recrystallized from hexane and filtered to give compound 3 as a pale yellow solid (3.2 g, 40%). $^1$H NMR (400 MHz, DMSO-d6) δ7.62 (s, 1H), 7.54 (d, J=2.4 Hz, 1H), 3.86 (s, 3H), 1.42 (s, 9H), 1.32 (s, 9H).

Preparation of Compound 4 (2,4-di-tert-butyl-5-nitrophenol)

To a stirred solution of compound 3 (3.0 g, 9.7 mmol) in MeOH (20 mL) was added NaOH (776 mg, 19.4 mmol) dissolved in H$_2$O (5 mL), and the reaction mixture was stirred at room temperature for 5 h and acidified with aq.2N HCl to pH 2-3. The resulting precipitate was collected by suction filtration. The desired regioisomer, compound 4 (2.4 g, 98%) was obtained as pale yellow solid and used in the next step after drying under high vacuum. $^1$H NMR (400 MHz, CDCl$_3$) δ7.42 (s, 1H), 6.69 (s, 1H), 5.20 (s, 1H), 1.41 (s, 9H), 1.38 (s, 9H).

Preparation of Compound 5 (2,4-di-tert-butyl-5-nitrophenyl trifluoromethanesulfonate)

To a stirred solution of compound 4 (1.0 g, 4.0 mmol) in dichloromethane (15 mL) was added diisopropylethylamine (0.5 mL) and triflic anhydride (2.24 mL, 8.0 mmol) at 0° C. drop wise. The resulting mixture was allowed to warm to RT and stirred overnight. The reaction mixture was diluted with dichloromethane (20 mL) and washed with water and saturated sodium bicarbonate. The organic phase was dried over Na$_2$SO$_4$ and concentrated. The residue was purified by a silica gel column chromatography using 10-40% ethyl acetate in hexanes to afford triflate intermediate 5 as pale yellow solid (1.2 g, 80%). $^1$H NMR (400 MHz, CDCl$_3$) δ7.67 (s, 1H), 7.37 (s, 1H), 1.45 (s, 9H), 1.42 (s, 9H). $^{19}$F NMR (376 MHz, CDCl$_3$) δ−73.94 (s).

Preparation of Compound 7 (2-(2,4-di-tert-butyl-5-nitrophenoxy)ethanol)

Compound 4 (1.0 g, 4.0 mmol) was taken up in DMF (5 mL) and potassium carbonate (1.0 g) and bromoethanol, 6 (2 mL) were added and the mixture was stirred at 95-100° C. in a sealed tube for 48 h. The reaction mixture was cooled, filtered and the filtrate was washed with water and extracted with ethyl acetate. The organic layer was concentrated and purified by silica gel column chromatography using 50-100% ethyl acetate in hexanes to afford compound 7 as yellow solid (800 mg, 68%). $^1$H NMR (400 MHz, CDCl$_3$) δ7.45 (s, 1H), 6.82 (s, 1H), 4.15-4.07 (m, 2H), 4.07-3.99 (m, 2H), 1.84-1.74 (m, 1H), 1.41 (s, 9H), 1.39 (s, 9H).

Preparation of Compound 8 (1,2-bis(2,4-di-tert-butyl-5-nitrophenoxy)ethane)

Compound 7 (800 mg, 2.70 mmol) was taken in dry THF and sodium hydride (260 mg, 10.8 mmol) was added at 0° C. The reaction mixture was stirred for 20 min and the triflate, 5 (1.0 g, 2.70 mmol) dissolved in THF (5 mL) was added slowly drop wise. The resulting reaction mixture was allowed to warm up to RT and stirred overnight. Quenched with addition of water (20 mL) and extracted with ethyl acetate. The organic layer was dried and concentrated and then purified by silica gel column chromatography to afford the dimer 8 as pale yellow solid (1.20 g, 84%). $^1$H NMR (400 MHz, CDCl$_3$) δ7.47 (s, 2H), 6.87 (s, 2H), 4.38 (s, 4H), 1.40 (s, 18H), 1.38 (s, 18H).

Preparation of Ivacaftor Dimer, Compound 10 (N,N'-((ethane-1,2-diylbis(oxy))bis(2,4-di-tert-butyl-5,1-phenylene))bis(4-oxo-1,4-dihydroquinoline-3-carboxamide))

Compound 8 (1.2 g, 2.3 mmol) was dissolved in the mixture of methanol (10 mL) and ethyl acetate (10 mL) and hydrogenated with 10% Pd-C using usual hydrogenation procedure. The reaction mixture was filtered over a Celite® bed and the Celite® was washed with plenty of methanol. The combined filtrate and washings were concentrated to give diamine which was taken in 2-Me-THF (40 mL) and was added, 4-oxo-1,4-dihydroquinoline-3-carboxylic acid, 9 (1.0 g, 5.3 mmol) followed by T3P 50% solution in 2-MeTHF (15 mL) and heated to 50° C. overnight. The reaction mixture was cooled to RT and solvents were removed under reduced pressure and purified by silica gel column chromatography using 10% methanol in dichloromethane. The product, 10 was obtained as off-white solid (605 mg, 35%). $^1$H NMR (400 MHz, DMSO-d$_6$) δ12.88 (s, 2H), 11.94 (s, 2H), 8.87 (s, 2H), 8.30 (d, J=8.1 Hz, 2H), 7.77 (t, J=7.5 Hz, 2H), 7.71 (d, J=8.3 Hz, 2H), 7.48 (t, J=7.4 Hz, 2H), 7.37 (s, 2H), 7.25 (s, 2H), 1.39 (s, 18H), 1.34 (s, 18H). ESMS: calculated, 810.44 (exact mass) and found: 811.4 (M+H) and 833.3 (M+Na). HPLC: 98% at 210 nm and 99% at 254 nm RT: 20.084 min. (Agilent 1100 LC, Chiracel OD-RH 4.6*150 mm, Sum; 0.5 mL/min, 40'C M.P.A:0.1% AA in H$_2$O M.P.B:0.1% AA in ACN). Melting point: Decomposed at 260° C. (turned black)

Example 2: Metabolism, Solubility, and Cystic Fibrosis Transmembrane Regulator (CFTR) Potentiator Effects of the Compound of Formula I (Compound 10)

Evaluation of Metabolic Stability of the Compound of Formula I and Ivacaftor

The compound of Formula I (Compound 10) (1 uM) and ivacaftor (1 uM) were incubated with human liver microsomes (1 mg/mL protein/mL) in the presence of NADPH generating system (NADP (1 mM, ph7, glucose-6-phosphate (5 mM ph 7.4) and glucose-6-phosphate dehydrogenase (1 Unit/mL) for 0, 30, 60, and 120 minutes. Remaining substrate was measured by LC-MS/MS. Concentration of the test article was converted to percent drug remaining relative to the concentration of the test article at Time Zero.

Results from the study demostrate the compound of Formula I is metabolically stable, i.e., drug was not lost to metabolism, and it does not revert back to ivacaftor. The study also demonstrates that almost 70% of ivacaftor is metabolized when incubated with human liver microsomes (Table 1).

TABLE 1

Metabolism of ivacaftor and the compound of Formula I (1 µM) in human liver microsomes

| Substrate | Time (min) | Peak area | Substrate loss (%) | Substrate remaining (%) | Half-life estimated from single exponential decay (min) | Estimated in vitro intrinsic clearance (µL/min/mg protein) |
|---|---|---|---|---|---|---|
| ivacaftor | 0 | 299000 | NA | 100 | 65.4 | 10.6 |
| | 30 | 208000 | 30.4 | 69.6 | | |
| | 60 | 152000 | 49.1 | 50.9 | | |
| | 120 | 91100 | 69.5 | 30.5 | | |
| Compound of Formula I | 0 | 335000 | NA | 100 | >120 | <5.78 |
| | 30 | 362000 | No loss | 108 | | |
| | 60 | 360000 | No loss | 107 | | |
| | 120 | 402000 | No loss | 120 | | |

Values are the mean of duplicate determinations and are rounded to three significant figures.
Percentages < 100% are rounded to one decimal point and percentages ≥ 100% are rounded to the nearest whole number.

Evaluation of Solubility of of the Compound of Formula I and Ivacaftor

Figure 1B:
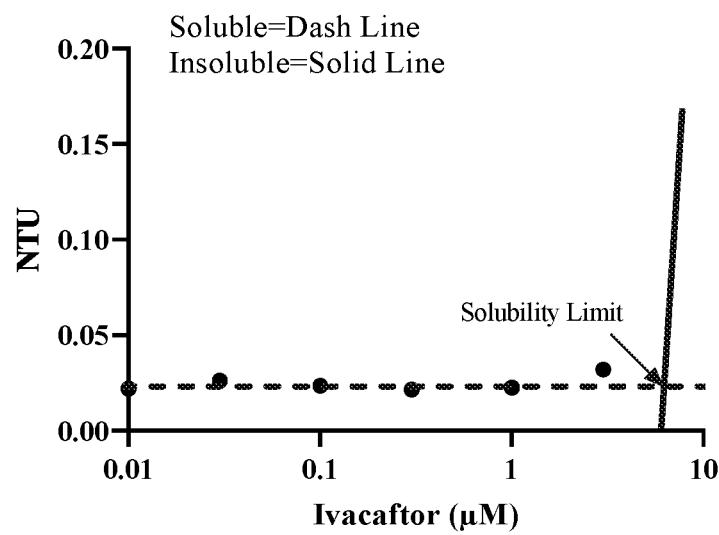

Solubility of the compound of Formula I (Compound 10) and ivacaftor was evaluated in HEPES-buffered physiological saline solution (HB-PS) with 0.3% DMSO. Solubility was measured as absence of turbidity using micropartic-ualtes light-scattering technology in nephelometer and output expressed as nephelometry turbidity units (NTU). The HEPES buffer with 0.3% DMSO was the media used for the Ussing Chamber assays as described below. Concentrations of Compound 10 and ivacaftor tested in duplicate were 0, 0.01, 0.03, 0.1, 0.3, 1, 3, 10, 30 µM. The NIST traceable reference standard at 0, 0.2, 0.6 and 1 NTU were measured in duplicate as a reference standard for turbidity. The NTU values were plotted against the concentrations of Compound 10 and ivacaftor. The solubility limits were interpolated from their respective solubility and turbidity plots, as shown in FIGS. 1A and 1B.

The solubility limit of the compound of Formula I in HB-PS wth 0.3% DMSO was calculated to be 0.137 µM. The solubility of ivacaftor ws calculated to be 7.864 µM. The compound of Formula I is 57.4 times less soluble compared to ivacaftor.

Evaluation of CFTR Potentiator Activity of the Compound of Formula I and Ivacaftor Chloride ion channel potentiator activity of the compound of Formula I (Compound 10) and ivacaftor was evaluated in monlayer cultures of human primary bronchial epithelia obtained from donors with the homozygous F508del CFTR missense mutation (CFhBE) using Ussing assay technology.

The Ussing chamber assay is a well-established method for measurement of transport across epithelia of a wide variety of transport substrates (Clark, American Journal of Physiology.Gastrointestinal and liver Physiology, 2009, 296, G1151-1166). The Ussing half-chambers permit both apical and basolateral surfaces of an epithelium to be exposed to identical solutions, eliminating the chemical concentration gradient for movement of molecules across the epithelium. Under these symmetric solution conditions, the epithelium generates a transepithelial potential by activity of ion selective channels and active transport processes asymmetrically distributed in apical and basolateral membranes. The epithelium is maintained at a potential difference of 0 mV. The negative feedback circuit used for controlling the potential difference at 0 mV is called a voltage clamp circuit. Any current generated by the voltage clamp to maintain the transepithelial potential at 0 mV can arise only from biological active transport processes in the epithelial cells and the current (called short circuit current ($I_{SC}$)) is a direct measure of these processes. Efflux of chloride to the apical surface is enabled by opening of apical CFTR channels, which allows water to move to the cellular surface and keep the tissue hydrated.

Figure 2A:
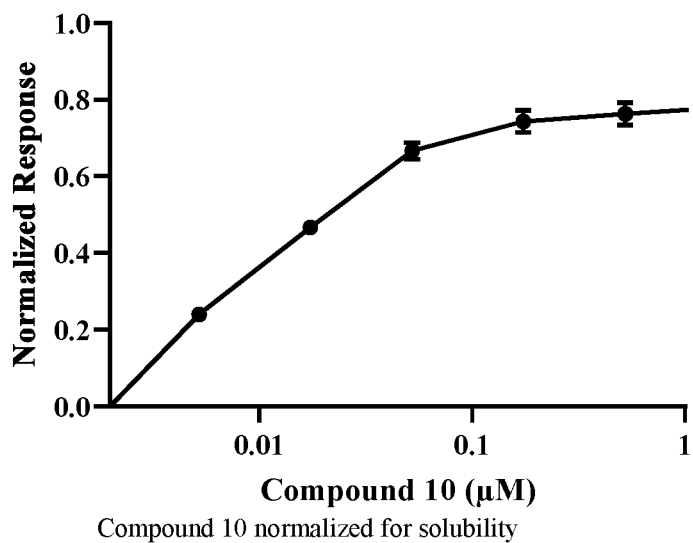
FIG. 2A and FIG. 2B show the potentiator response of the compound of Formula I (Compound 10) and ivacaftor, respectively.
Figure 2B:
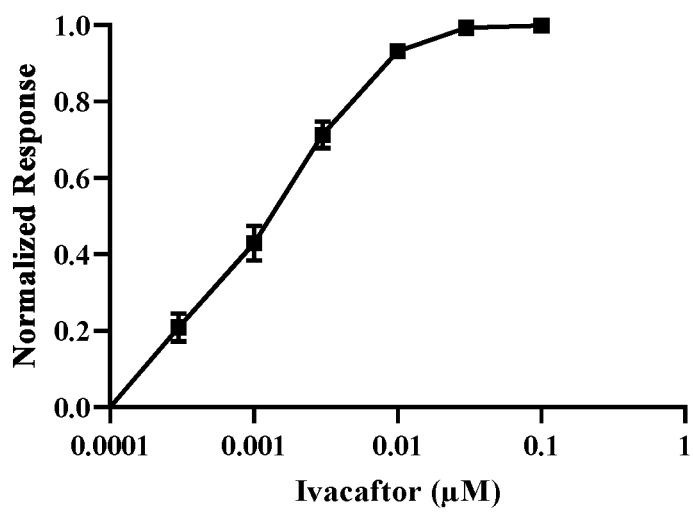

The compound of Formula I (Compound 10) is a potentiator of F508del CFTR and its potentiator response is similar to ivacaftor, as shown in FIGS. 2A and 2B.

Based on solubility difference between the compound of Formula I and ivacaftor, the compound of Formula I is potentially at least 15-times more potent than ivcaftor.

The compound of Formula I (Compound 10) potentiated F508del CFTR and appears to remain stable longer than ivacftor, as seen in FIGS. 2A and 2B. Accordingly, it is believed that cystic fibrosis patients should experience improvement in their lung function longer than experienced with ivacaftor.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound having the formula:

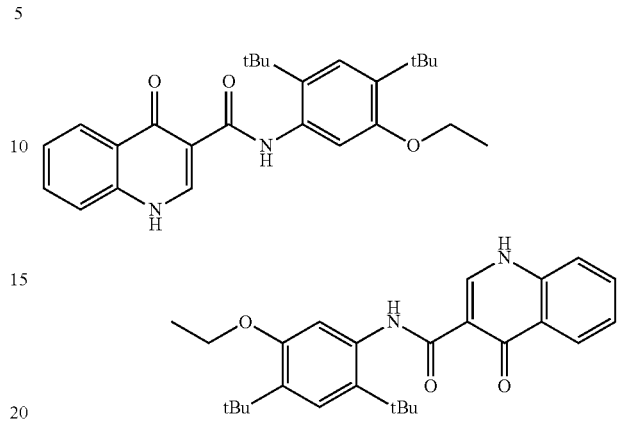

or a pharmaceutically acceptable salt, hydrate, solvate or complex thereof.

2. The compound of claim 1, having the formula:

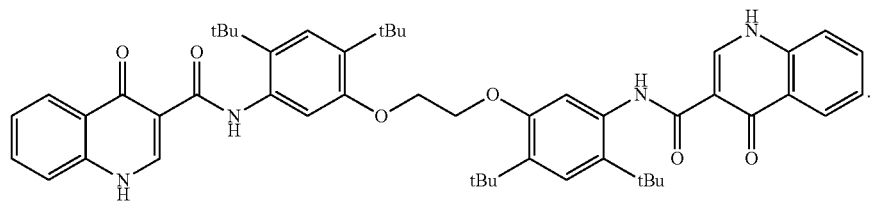 [SMILES: CC(C)(C)c1cc(C(C)(C)C)c(OCCOc2cc(NC(=O)c3c[nH]c4ccccc4c3=O)c(C(C)(C)C)cc2C(C)(C)C)cc1NC(=O)c1c[nH]c2ccccc2c1=O]

3. A pharmaceutical composition comprising a compound of claim 1, and a pharmaceutically acceptable excipient.

4. The pharmaceutical composition of claim 3, wherein said composition is formulated for oral delivery.

5. The pharmaceutical composition of claim 3, in a tablet, lozenge or capsule form.

6. The pharmaceutical composition of claim 3, in a tablet form.

7. A method of treating cystic fibrosis in a subject in need thereof, said method comprising administering to said subject an effective amount of a compound of claim 1.

8. A method in accordance with claim 7, wherein said compound is administered orally.

9. A method in accordance with claim 7, wherein said compound is administered in the form of a tablet, capsule or lozenge.

10. A method of treating cystic fibrosis in a subject in need thereof, said method comprising administering to said subject an effective amount of a composition according to claim 3.

11. A method in accordance with claim 10, wherein said subject is a human having a mutation in their cystic fibrosis transmembrane conductance regulator (CFTR) protein selected from the group consisting of E56K, G178R, S549R, K1060T, G1244E, P67L, E193K, G551D, A1067T, S1251N, R74W, L206W, G551S, G1069R, S1255P, D110E, R347H, D579G, R1070Q, D1270N, D110H, R352Q, S945L, R1070W, G1349D, R117C, A455E, S977F, F1074L, R117H, S549N, F1052V, and D1152H.

12. A method of treating cystic fibrosis in a subject in need thereof, said method comprising administering to said subject an amount of a compound of claim 1, and a second therapeutic agent.

13. A method in accordance with claim 12, wherein said second therapeutic agent is selected from the group consisting of lung surfactants, respiratory stimulants, 5-HT4 receptor agonists and agents for treating respiratory depression.

14. A method in accordance with claim 13, wherein said second therapeutic agent is lumacaftor.

* * * * *